(12) United States Patent
Ouchi

(10) Patent No.: US 6,527,705 B1
(45) Date of Patent: Mar. 4, 2003

(54) FULLY-SWALLOWABLE ENDOSCOPIC SYSTEM

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 75 days.

(21) Appl. No.: 09/588,467

(22) Filed: Jun. 6, 2000

(30) Foreign Application Priority Data

Jun. 7, 1999 (JP) .............................. 11-160028

(51) Int. Cl.⁷ ............................... A61B 1/005
(52) U.S. Cl. ................ 600/139; 600/141; 600/143; 600/146; 600/130
(58) Field of Search ................ 600/101, 109, 600/128, 130, 136, 139, 141, 143, 151, 152, 146; 348/65, 68, 71, 74

(56) References Cited

U.S. PATENT DOCUMENTS

| | | | |
|---|---|---|---|
| 4,633,304 A | * 12/1986 | Nagasaki | 600/109 |
| 5,398,670 A | * 3/1995 | Ortiz et al. | 600/109 |
| 5,595,565 A | * 1/1997 | Treat et al. | 600/101 |
| 5,604,531 A | * 2/1997 | Iddan et al. | 600/109 |
| 5,662,587 A | * 9/1997 | Grundfest et al. | 600/114 |
| 6,162,171 A | * 12/2000 | Ng et al. | 600/0 |
| 6,240,312 B1 | * 5/2001 | Alfano et al. | 600/476 |

FOREIGN PATENT DOCUMENTS

| | | | |
|---|---|---|---|
| GB | Wo 98/11816 | * | 3/1998 |
| JP | 64-4450 | | 1/1989 |
| JP | 64-76822 | | 3/1989 |
| JP | 3-9705 | | 1/1991 |
| JP | 4-144533 | | 5/1992 |
| JP | 6-114064 | | 4/1994 |
| JP | 7-111985 | | 5/1995 |

* cited by examiner

Primary Examiner—John P. Leubecker
(74) Attorney, Agent, or Firm—Greenblum & Bernstein, P.L.C.

(57) ABSTRACT

A fully-swallowable endoscopic system includes a rod-shaped endoscope body which can be swallowed entirely by a patient to be examined so as to be placed in a body cavity, the rod-shaped endoscope body including two bendable portions respectively provided close to the opposite ends of the rod-shaped endoscope body and each being bendable along a curve of the body cavity, and an external device provided separately from the rod-shaped endoscope body having no mechanical connection with the rod-shaped endoscope body. The rod-shaped endoscope body is provided therein with at least one light emitter, at least one observing system, a transmitter for transmitting a radio wave which carries an image formed by the observing system, and a power supplying device. The external device includes a receiver for receiving the radio wave which carries the image.

19 Claims, 9 Drawing Sheets

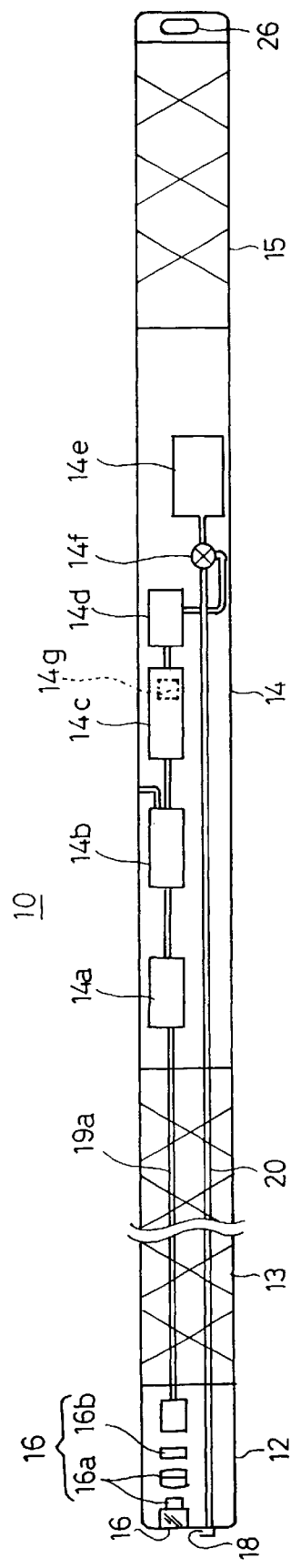
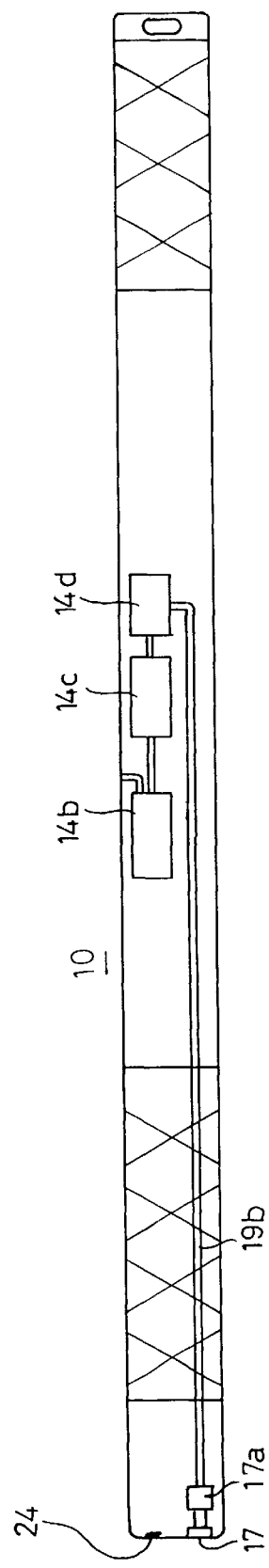
Fig.2
Fig.3

FULLY-SWALLOWABLE ENDOSCOPIC SYSTEM

BACKGROUND OF THE INVENTION

1. Field of the Invention

The present invention relates to a fully-swallowable endoscopic system which can be retained in the patient's body for a long time, wherein few blind spots occur in an endoscopy examination.

2. Description of the Related Art

In an endoscopy examination, in general, an insertion portion connected to an operation portion is introduced into a patient's body through his or her mouth to observe a target inner part of the body. In the case of observing an inner part of a largely-bent tubular passage in a body such as part of the large intestine, the occurrence of blind spots in the endoscopy examination cannot be avoided.

The insertion portion of the endoscope must be sometimes inserted and retained in the body for a long time to observe the progress of a diseased part within the body or obtain and/or record somatoscopic information of a patient under ordinary every-day living conditions. However, the insertion and retainment of the endoscope in the body through the patient's mouth causes the patient to suffer from significant pain.

To relieve pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member the night before the day of examination, so that the soft ball is discharged from the patient's anus the next day. An operator pulls or moves the tip end and the tail end of the flexible continuous member to thereby move or guide the capsule connected to the intermediate portion of the flexible continuous member.

In the capsule type of endoscope described above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is generally difficult to control the position of the endoscope when in the form of a capsule.

SUMMARY OF THE INVENTION

It is an object of the present invention to provide a fully-swallowable endoscopic system which can relieve a patient to be examined from pain and which makes it possible to observe the target inner part of the body reliably and precisely.

To achieve the object mentioned above, according to the present invention, a fully-swallowable endoscopic system is provided, which includes a rod-shaped endoscope body which can be swallowed entirely by a patient to be examined so as to be placed in a body cavity, the rod-shaped endoscope body including two bendable portions respectively provided close to the opposite ends of the rod-shaped endoscope body and each being bendable along a curve of the body cavity; and an external device provided separately from the rod-shaped endoscope body having no mechanical connection with the rod-shaped endoscope body. The rod-shaped endoscope body is provided therein with at least one light emitter, at least one observing system, a transmitter for transmitting a radio wave which carries an image formed by the observing system, and a power supplying device. The external device includes a receiver for receiving the radio wave which carries the image.

Preferably, the rod-shaped endoscope body includes a flexible portion which bends when an external force is applied thereto, the flexible portion being positioned between the two bendable portions to connect the two bendable portions, and wherein each of the two bendable portions includes a bending portion which can be radio-controlled to bend by an operation of the external device. The rod-shaped endoscope body is provided therein with a radio-controlled driving device which receives a radio operational signal transmitted from the external device to bend the bending portion in accordance with the radio operational signal, and the external device includes an operational portion which is operated to transmit the radio operational signal to the radio-controlled driving device.

In an embodiment, the rod-shaped endoscope body includes more than one light emitter and more than one observing system which are positioned at different locations.

Preferably, the radio-controlled driving device includes a plurality of drive wires made of a shape memory alloy, and a selective-heating device which selectively heats the plurality of drive wires to bend the bending portion.

The power supplying device can be a built-in battery.

In an embodiment, the external device includes a microwave transmitter for transmitting a microwave to the rod-shaped endoscope body, wherein the power supplying device converts the microwave into electrical current to supply the electrical current to the rod-shaped endoscope body.

Preferably, the observing system includes an objective optical system and a CCD image sensor.

Preferably, the external device includes a monitor which visually indicates the image.

According to another aspect of the present invention, a fully-swallowable endoscopic system is provided, which includes a rod-shaped endoscope body having a first bending portion, a flexible portion and a second bending portion which are arranged in that order; and a radio controller for manipulating each of the first and second bending portions so as to bend by radio-control. The rod-shaped endoscope body is provided therein with at least one light emitter for illuminating a target inner part of a living body, at least one image pick-up device for taking an image of the target inner part illuminated by the at least one light emitter, and a transmitter for transmitting a radio wave which carries the image taken by the image pick-up device.

In an embodiment, the rod-shaped endoscope body further includes a first hard portion fixed to one of the opposite ends of the rod-shaped endoscope body, and one of the at least one light emitter and one of the at least one image pick-up device are fixed to the first hard portion.

Preferably, the rod-shaped endoscope body further includes a second hard portion fixed to the other of the opposite ends of the rod-shaped endoscope body, and another of the at least one light emitter and another of the at least one image pick-up device are fixed to the second hard portion.

Preferably, the radio controller includes a monitor and a receiver for receiving the radio wave to indicate the image on the monitor.

In an embodiment, the radio controller further includes a second transmitter for transmitting a microwave to the rod-shaped endoscope body, and the rod-shaped endoscope body is provided therein with a power supplying device which receives the microwave to convert the microwave into electrical current which is to be used as a power source of the rod-shaped endoscope body.

The present disclosure relates to subject matter contained in Japanese Patent Application No.11-160028 (filed on Jun. 7, 1999) which is expressly incorporated herein by reference in its entirety.

BRIEF DESCRIPTION OF THE DRAWINGS

The invention will be discussed below in detail with reference to the drawings, in which:

FIG. 2 is a schematic cross sectional view of the first embodiment of the rod-shaped endoscope body, according to the present invention;

FIG. 3 is a schematic cross sectional view of the rod-shaped endoscope body shown in FIG. 2, taken along a different plane;

DESCRIPTION OF THE PREFERRED EMBODIMENTS

Figure 1:
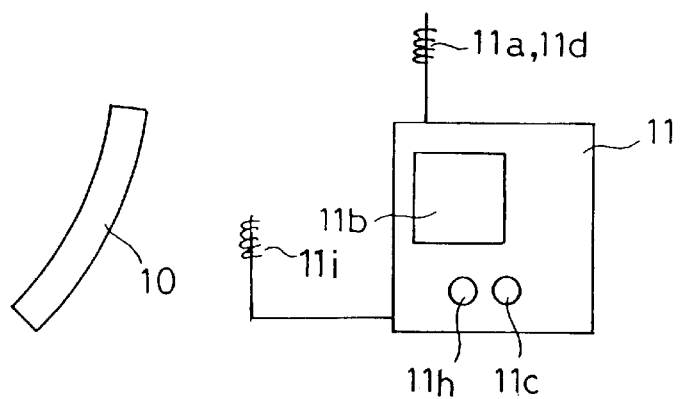
FIG. 1 is a schematic view of an embodiment of a fully-swallowable endoscopic system having a rod-shaped endoscope body and an external device, according to the present invention.
Figure 7:
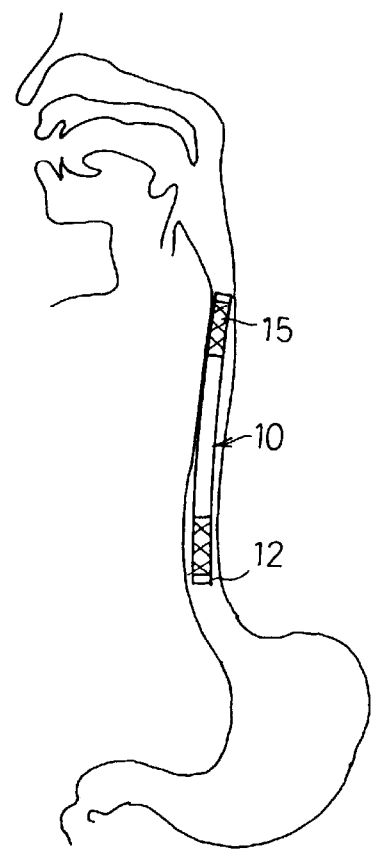
FIG. 7 is an explanatory view of the rod-shaped endoscope body which is positioned in a human body, showing a state where the rod-shaped endoscope body is swallowed to reach the esophagus.

FIG. 1 shows an embodiment of a fully-swallowable endoscopic system which includes a rod-shaped endoscope body 10 and an external device 11. A patient to be examined swallows the rod-shaped endoscope body 10 before an endoscopic examination is performed with the endoscope 10. The external device 11 functions as a wireless controller (radio controller) and a power supply for the endoscope 10.

Figure 4:
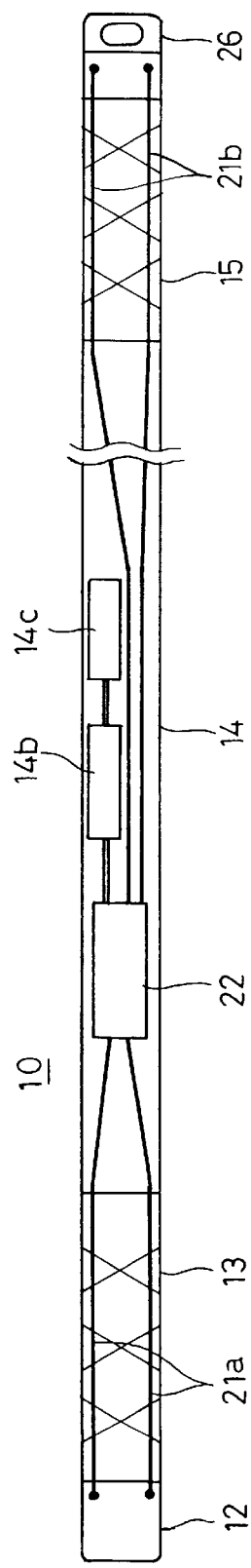
FIG. 4 is a schematic cross sectional view of the rod-shaped endoscope body shown in FIG. 2, showing a radio-controlled bending device thereof.

FIGS. 2 through 4 show the first embodiment of the rod-shaped endoscope body 10. The rod-shaped endoscope body 10 is provided with a hard portion (unbendable portion) 12, a first bending portion 13, a flexible portion 14, a second bending portion 15 and a hooked portion 26, in this order from the front end (the left end as viewed in FIG. 2). The first bending portion 13 and the flexible portion 14 constitute a bendable portion, and the second bending portion 15 and the flexible portion 14 constitute another bendable portion. The rod-shaped endoscope body 10 is entirely covered by an elastic covering 30 (see FIG. 18) whose outer surface is smooth and well-slidable. The hard portion 12 is made of a hard material (e.g., a hard plastic) which is not macroscopically deformable. The flexible portion 14 is designed to be bendable along the shape of a digestive tract when it is inserted in a body cavity.

The hard portion 12 is provided therein with an observing system 16, an illumination window 17 and an air supply port 18. The observing system 16 includes an objective optical system 16a and a CCD image sensor 16b. The flexible portion 14 is provided therein with an amplifier circuit 14a, a transmitter/receiver device 14b, a power supplying device 14c, a control circuit 14d, a compressed air tank 14e and a microwave receiver 14g. The CCD image sensor 16b is connected to the amplifier circuit 14a via a signal line 19a which extends within the first bending portion 13. The amplifier circuit 14a is connected to the transmitter/receiver device 14b, which is positioned in the flexible portion 14. The hard portion 12 is provided therein with an LED (light emitter) 17a which is secured to the illumination window 17. The LED 17a is connected to the control circuit 14d via a signal line 19b which extends within the first bending portion 13 (see FIG. 3).

The air supply port 18 is connected to the front end of an air supply tube 20 which extends within the hard portion 12, the first bending portion 13 and the flexible portion 14. The rear end (inner end) of the air supply tube 20 is connected to the compressed air tank 14e. The compressed air tank 14e is provided with a valve 14f which is controlled to open or shut by the control circuit 14d. The power supplying device 14c is connected to the transmitter/receiver device 14b and the control circuit 14d. The power supplying device 14c converts a microwave received by the microwave receiver 14g into electrical current to supply the same to the transmitter/receiver device 14b and the control circuit 14d. The microwave received by the microwave receiver 14g is transmitted from the external device 11.

Figure 18:
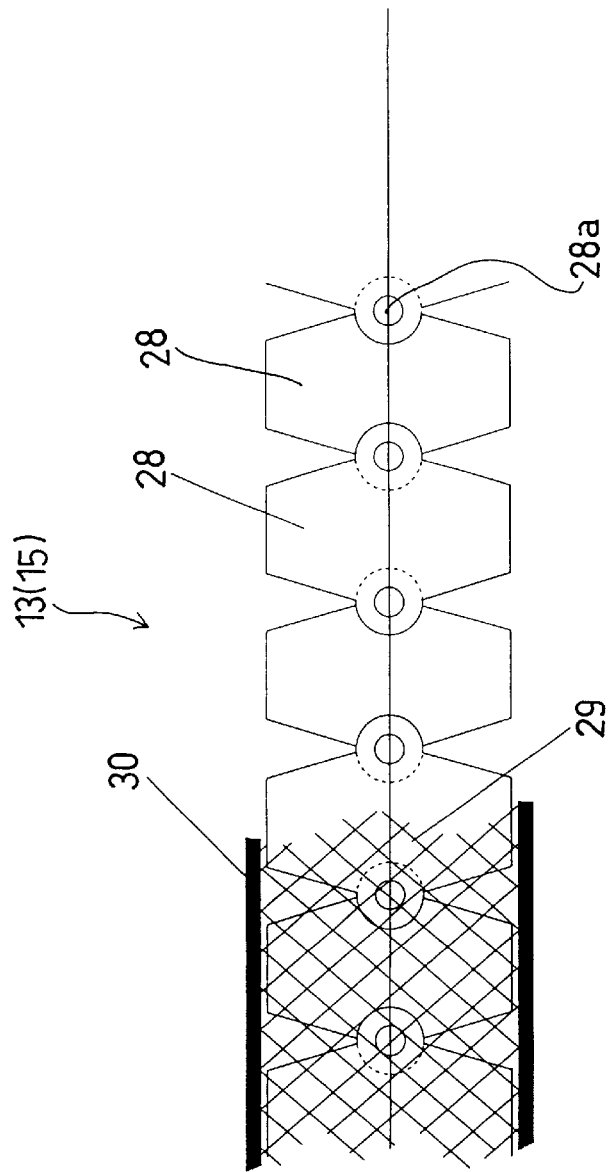
FIG. 18 is a schematic side view of part of the first embodiment of the bending portion, with parts omitted for clarity, in the case where the bending portion is designed to be bendable in a single plane.

FIG. 18 shows part of the first embodiment of each of the first and second bending portions 13 and 15 in the case where each bending portion is designed to be bendable in a single plane. The first embodiment of each bending portion is provided with an articulated series of ring joints 28. Adjacent ring joints 28 are connected with each other by a shaft 28a so that each of the adjacent ring joints 28 can rotate about the shaft 28a. All the shafts 28a are parallel to one another so as to lie in a common plane. The articulated series of ring joints 28 having such a structure is covered by a steel wired tube 29. This steel wired tube 29 is covered by the aforementioned elastic covering 30. Each of the first and second bending portions 13 and 15 is designed to be more flexible and bendable than the flexible portion 14 to bend from the flexible portion 14. Namely, each of the opposite ends of the rod-shaped endoscope body 10 is designed as a bendable portion.

The rod-shaped endoscope body 10 is provided therein with a plurality of bendable drive wires (two wires in the first embodiment of the first bending portion 13) 21a which extend within the first bending portion 13 and the flexible portion 14 (see FIG. 4). Each drive wire 21a is made of a shape memory alloy (SMA) which bends when supplied with electrical current to be heated thereby. The rod-shaped endoscope body 10 is further provided therein with a selective-heating device 22 which is connected to the transmitter/receiver device 14b (see FIG. 4). The drive wires 21a, the selective heating device 22, and the transmitting/receiving device 14b constitute a radio-control led driving device. The front ends (outer ends) of the drive wires 21a are each secured to the hard portion 12, while the rear ends (inner ends) of the drive wires 21a are each secured to the selective-heating device 22.

The two drive wires 21a are diametrically arranged at opposite sides of the axis of the cylindrical first bending portion 13. The selective-heating device 22 is a circuit which selectively supplies electrical current to the two drive wires 21a to heat the same in accordance with control signals output from the transmitter/receiver device 14b, which makes it possible to bend the first bending portion 13 in a plane in which the two drive wires 21a lie.

Figure 17:
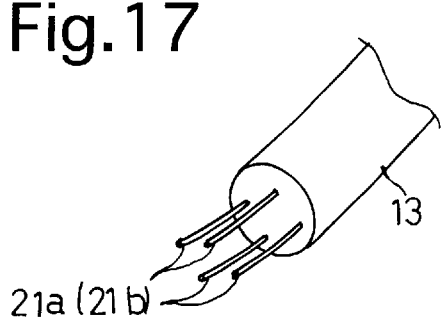
FIG. 17 is an explanatory view of part of the second embodiment of the bending portion of the rod-shaped endoscope body, showing an arrangement of the bendable drive wires provided in the bending portion.
Figure 19:
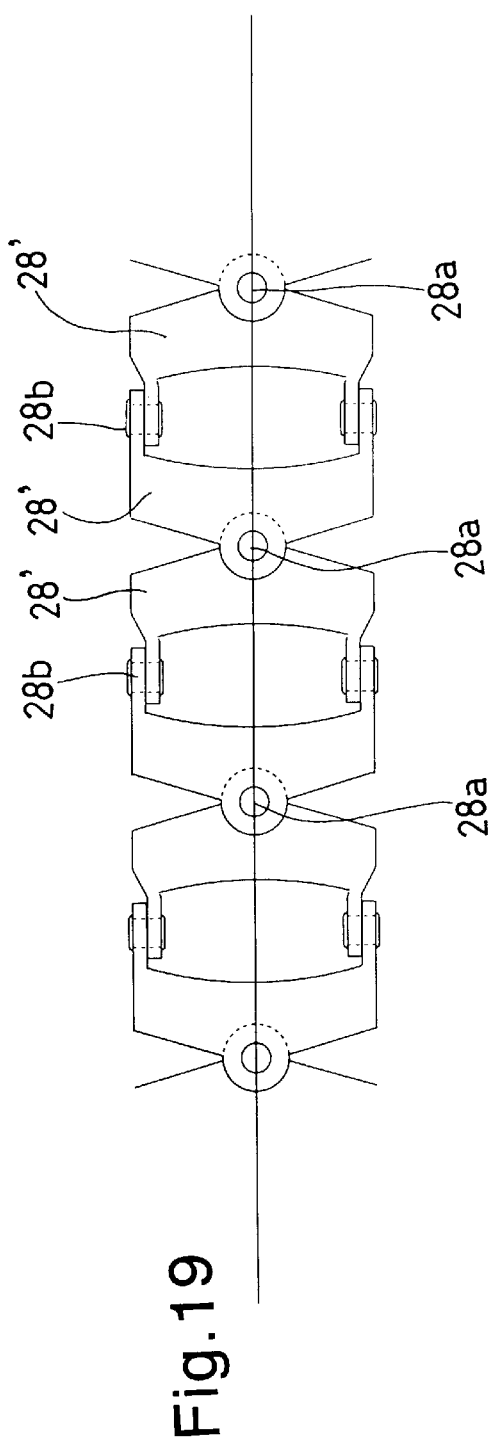
FIG. 19 is a schematic side view of part of the second embodiment of the bending portion, in the case where the bending portion is designed to be bendable in two planes perpendicular to each other.

When it is required that the first bending portion 13 be bendable only in a single plane, it is sufficient that the rod-shaped endoscope body 10 be provided with the first embodiment of the first bending portion 13, as shown in FIG. 18, which can bend only in a single plane. When it is required that the first bending portion 13 be bendable in two planes perpendicular to each other, the first bending portion 13 needs to have a structure such as shown in FIG. 19. FIG. 19 shows part of the second embodiment of each of the first and second bending portions 13 and 15 in the case where it is designed to be bendable in two planes perpendicular to each other. The second embodiment of each bending portion is provided with an articulated series of ring joints 28'. Adjacent ring joints 28' are connected with each other by a first shaft 28a or a second shaft 28b so that each of the adjacent ring joints 28' can rotate about each of the shafts 28a and 28b. The first and second shafts 28a and 28b extend in directions perpendicular to each other and are alternately arranged. In FIG. 19, neither the steel wired tube 29 nor the aforementioned elastic covering 30 is illustrated for clarity of illustration. In the second embodiment of the first bending portion 13, four bendable drive wires 21a extend within the first bending portion 13 and the flexible portion 14 (see FIG. 17). The front ends (outer ends) of the four drive wires 21a are each secured to the hard portion 12 at 90 intervals about the axis of the hard portion 12. The rear ends (inner ends) of each pair of drive wires 21a which are diametrically opposite to each other are secured to the selective-heating device 22. In the second embodiment of the first bending portion 13, although only two drive wires 21a are shown in FIG. 4, the remaining two drive wires 21a are provided in a similar manner.

Similar to the first bending portion 13, the rod-shaped endoscope body 10 is provided therein with another plurality of bendable drive wires (two wires in the first embodiment of the second bending portion 15) 21b which extend within the second bending portion 15 and the flexible portion 14 (see FIG. 4). Each drive wire 21b is made of a shape memory alloy (SMA) which bends when supplied with electrical current to be heated thereby. The front ends (inner ends) of the drive wires 21b are each secured to the selective-heating device 22, while the rear ends (outer ends) of the drive wires 21b are each secured to the hooked portion 26. The drive wires 21b, the selective heating device 22, and the transmitting/receiving device 14b constitute a radio-controlled driving device.

The two drive wires 21b are diametrically arranged at opposite sides of the axis of the cylindrical second bending portion 15. The selective-heating device 22 is a circuit which selectively supplies electrical current to the two drive wires 21b to heat the same in accordance with control signals output from the transmitter/receiver device 14b, which makes it possible to bend the second bending portion 15 in a plane in which the two drive wires 21b lie.

When it is required that the second bending portion 15 be bendable only in a single plane, it is sufficient that the rod-shaped endoscope body 10 be provided with the first embodiment of the second bending portion 15 as shown in FIG. 18 which can bend only in a single plane. When it is required that the second bending portion 15 be bendable in two planes perpendicular to each other, the second bending portion 15 needs to have a structure such as shown in FIG. 19, similar to the second embodiment of the first bending portion 13. In the second embodiment of the second bending portion 15, similar to the second embodiment of the first bending portion 13, four bendable drive wires 21b extend within the second bending portion 15 and the flexible portion 14 (see FIG. 17). The rear ends (outer ends) of the four drive wires 21b are each secured to the hooked portion 26. The front ends (inner ends) of each pair of drive wires 21*b* which are diametrically opposite to each other are secured to the selective-heating device 22. In the second embodiment of the second bending portion 15, although only two drive wires 21*b* are shown in FIG. 4, the remaining two drive wires 21*b* are provided in a similar manner.

Figure 12:
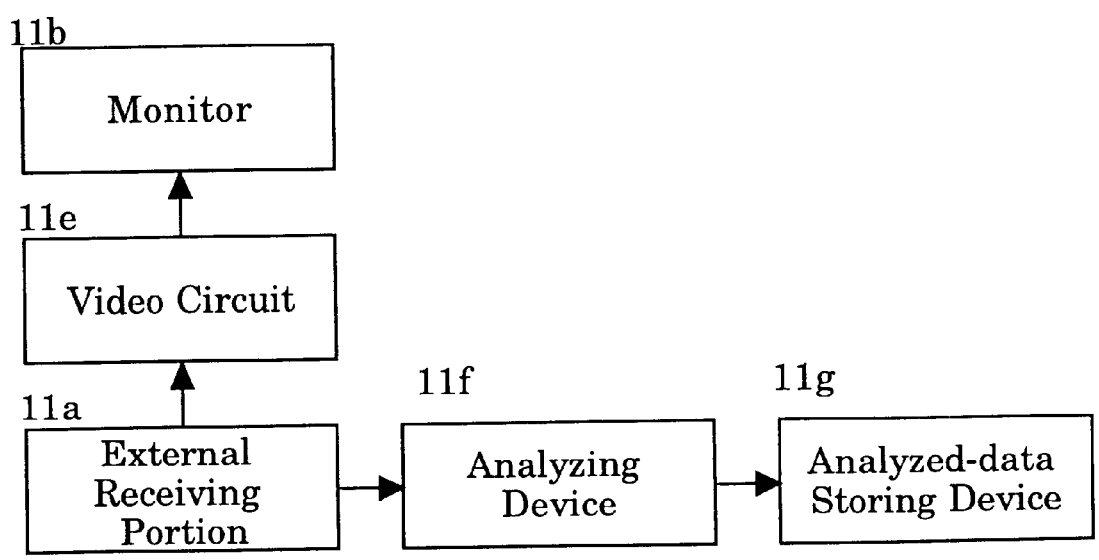
FIG. 12 is a block diagram of a process which is performed after the external device receives a signal output from the rod-shaped endoscope body.

The external device 11 shown in FIG. 1 is provided with an external receiving portion 11*a*, a monitor 11*b*, a bending portion controller portion (operational portion) 11*c*, an external transmitting portion 11*d*, a valve controlling portion 11*h* and a microwave transmitting portion (microwave transmitter) 11*i*. The external device 11 is further provided with a video circuit 11*e*, an analyzing device 11*f* and an analyzed-data storing device 11*g* (see FIG. 12). The external device 11 transmits the aforementioned microwave, which is used as a power supply for the rod-shaped endoscope body 10, from the microwave transmitting portion 11*i* to the rod-shaped endoscope body 10. This transmitted microwave is received by the microwave receiver 14*g* and is converted into electrical current by the power supplying device 14*c*. The power supplying device 14*c* supplies the electrical current to the transmitter/receiver device 14*b* and the control circuit 14*d*. By manually operating the bending portion controller portion 11*c* and the valve controlling portion 11*h* of the external device 11, radio operational signals for operating the first or second bending portion 13 or 15 and the valve 14*f* are generated by the external device 11 to be transmitted to the rod-shaped endoscope body 10 via the external transmitting portion 11*d*. The external receiving portion 11*a* receives image signals (radio waves) transmitted from the transmitter/receiver device 14*b*. The received image signals are displayed on the monitor 11*b* to be observed by an operator.

Figure 8:
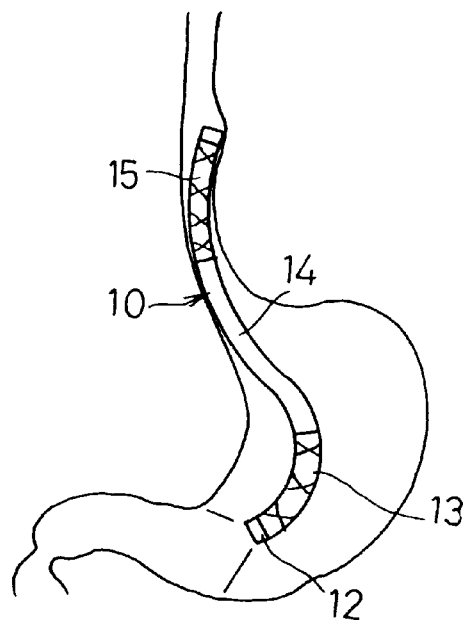
FIG. 8 is an explanatory view of the rod-shaped endoscope body which is positioned between the esophagus and the stomach, showing a state where the inside of the stomach can be observed with the rod-shaped endoscope body.
Figure 16:
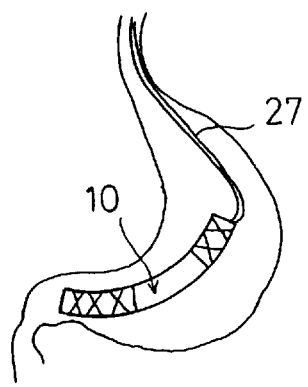
FIG. 16 is an explanatory view of the first embodiment of the rod-shaped endoscope body which is positioned in the stomach, showing a state where the rod-shaped endoscope body is forcibly pulled up by a pulling device having a hook engaging with a hole formed at the rear end of the rod-shaped endoscope body.

In the endoscope constructed as above, a patient to be examined swallows the rod-shaped endoscope body 10 entirely from the front end thereof, i.e., from the hard portion 12. After being swallowed entirely, the rod-shaped endoscope body 10 is radio-controlled to proceed gradually along an alimentary canal by peristalsis. When the hard portion 12 reaches the stomach as shown in FIG. 8, the second bending portion 15, which is positioned at the rear end of the rod-shaped endoscope body 10, can be fixed to an inner wall of the esophagus by bending the second bending portion 15. This makes it easy to observe the inside of the stomach with the rod-shaped endoscope body 10. In the case where the operator desires to forcibly push and pull the rod-shaped endoscope body 10 positioned in a body cavity, he or she only needs to use a pulling device 27 which is provided at the distal end thereof with a hook that is engageable with a hook-engaging hole formed on the hooked portion 26 (see FIG. 16). Depending upon the circumstances, the pulling device 27 can be in the form of: grasping forceps provided at the distal end thereof with a pair of claws which is used in the case where a foreign substance has to be pulled out of a body cavity of a baby or a child when he or she has swallowed the foreign substance, rat-teeth type forceps, basket type forceps used when a polyp is taken out after it is cut off an inner wall of a body cavity, forceps provided at the distal end thereof with a hook, etc. Once the rod-shaped endoscope body 10 reaches a target inner part of the body, it can be observed via the rod-shaped endoscope body 10 and at the same time the necessary information about a living body can be collected in a manner such as in the following description.

In the present embodiment of the fully-swallowable endoscopic system, the transmitter/receiver device 14*b* of the rod-shaped endoscope body 10 receives the radio operational signals transmitted from the external transmitting portion 11*d* of the external device 11 so that each of the fundamental operational elements of the rod-shaped endoscope body 10 can be radio-controlled by operating the external device 11. The power supplying device 14*c* supplies electrical current to the transmitter/receiver device 14*b* and the control circuit 14*d* by converting the received microwave into electrical current, so that the operator does not have to care about the remaining battery power of the rod-shaped endoscope body 10. This makes it possible to observe the target inner part of the body sufficiently.

The LED 17*a*, which receives power from the power supplying device 14*c* via the signal line 19*b* and the control circuit 14*d*, emits light outwardly through the illumination window 17. The object image upon which the illumination light is impinged is formed on the sensitive surface of the CCD image sensor 16*b* through the objective optical system 16*a*. The image signal supplied from the CCD image sensor 16*b* is amplified by the amplifier circuit 14*a*. This amplified image signal is transmitted from the transmitter/receiver device 14*b* to be subsequently received by the external receiving portion 11*a* of the external device 11. The image signal received by the external device 11 is processed by the video circuit 11*e* to be observed on the monitor 11*b* (see FIG. 12). The operator operates the bending portion controller portion 11*c* of the external device 11 to bend the first bending portion 13 or the second bending portion 15 via the selective-heating device 22, which is controlled by the radio operational signals transmitted from the external transmitting portion 11*d*, to thereby change the direction of the objective optical system 16*a* to observe the target inner part of the body. At this time, if an alimentary canal is made to inflate by sending the compressed air in compressed air tank 14*e* from the air supply port 18 to the alimentary canal via the air supply tube 20 by operating the valve controlling portion 11*h* of the external device 11 so that the transmitter/receiver device 14*b* receives radio operational signals transmitted from the external transmitting portion 11*d*, so as to operate the valve 14*f*, the distance between the hard portion 12 and the inner wall of the alimentary canal becomes large, which makes it easy to observe the inner wall of the alimentary canal.

A measuring device 24 for measuring information about a living body such as pH value, temperature, the amount of oxygen contained in blood, the hardness of the surface of cells, and the like, can be incorporated in the rod-shaped endoscope body 10 (see FIG. 3). In this case, the measured information can be transmitted from the transmitter/receiver device 14*b* to be received by the external receiving portion 11*a* of the external device 11. The received information can be analyzed and stored in the case where the analyzing device 11*f* analyzes the received information, and the analyzed-data storing device 11*g* stores the analyzed information (see FIG. 12).

Figure 5:
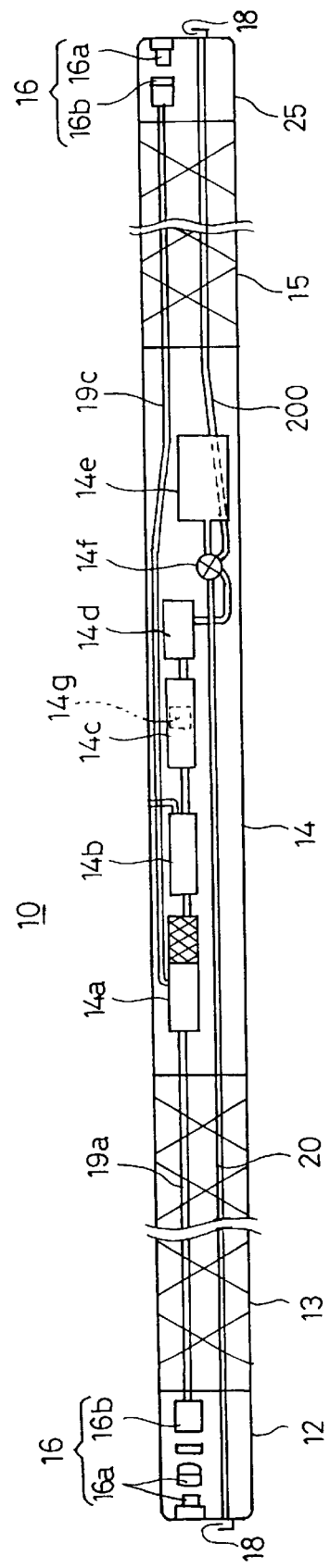
FIG. 5 is a schematic cross sectional view of the second embodiment of the rod-shaped endoscope body, according to the present invention.
Figure 6:
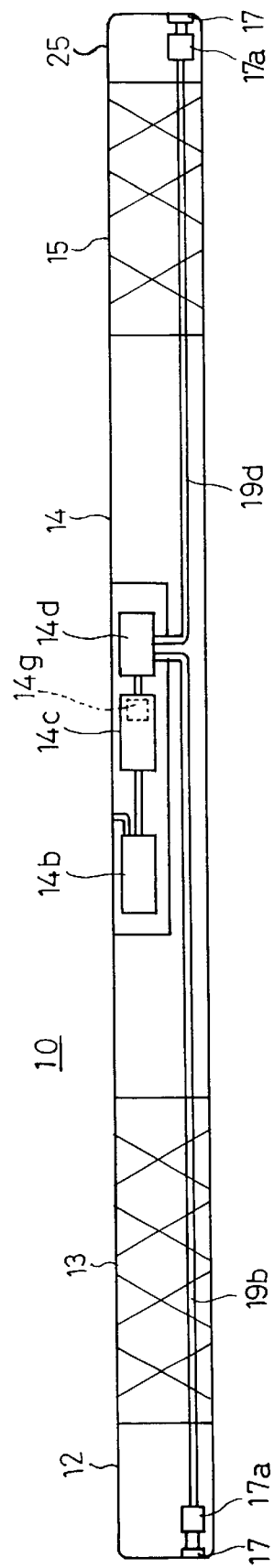
FIG. 6 is a schematic cross sectional view of the rod-shaped endoscope body shown in FIG. 5, taken along a different plane.

FIGS. 5 and 6 show the second embodiment of the rod-shaped endoscope body 10. The second embodiment of the rod-shaped endoscope body 10 is substantially identical to the first embodiment of the rod-shaped endoscope body 10 except that the latter is provided at the rear end thereof with the hooked portion 26 whereas the former is provided at the rear end thereof with a second hard portion 25. Accordingly, the second embodiment of the rod-shaped endoscope body 10 is provided with a hard portion (unbendable portion) 12, a first bending portion 13, a flexible portion 14, a second bending portion 15 and the second hard portion 25, in this order from the front end (the left end as viewed in FIG. 5). Similar to the hard portion 12, the second hard portion 25 is made of a hard material (e.g., a hard plastic) which is not macroscopically deformable and is provided therein with an observing system 16, an illumination window 17 and an air supply port 18. The observing system 16 includes an objective optical system 16a and a CCD image sensor 16b. The CCD image sensor 16b is connected to the amplifier circuit 14a via a signal line 19c which extends within the second bending portion 15. The amplifier circuit 14a is connected to the transmitter/receiver device 14b, which is positioned in the flexible portion 14. The second hard portion 25 is also provided therein with an LED (light emitter) 17a which is secured to the corresponding illumination window 17. The LED 17a in the second hard portion 25 is connected to the control circuit 14d via a signal line 19d which extends within the second bending portion 15 (see FIG. 6).

The air supply port 18 on the second hard portion 25 is connected to the rear end (outer end) of an air supply tube 200 which extends within the second hard portion 25, the second bending portion 15 and the flexible portion 14. The front end (inner end) of the air supply tube 200 is connected to the valve 14f of the compressed air tank 14e.

Figure 9:
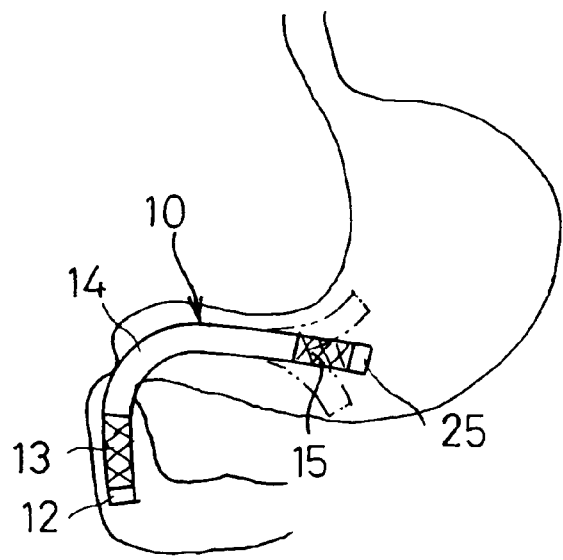
FIG. 9 is an explanatory view of the rod-shaped endoscope body shown in FIGS. 5 and 6 which is positioned between the stomach and the duodenum, showing a state where the front bending portion of the rod-shaped endoscope body further proceeds from the stomach to the duodenum so that the inside of the stomach can be observed by the observing system provided at the rear end of the rod-shaped endoscope body.
Figure 10:
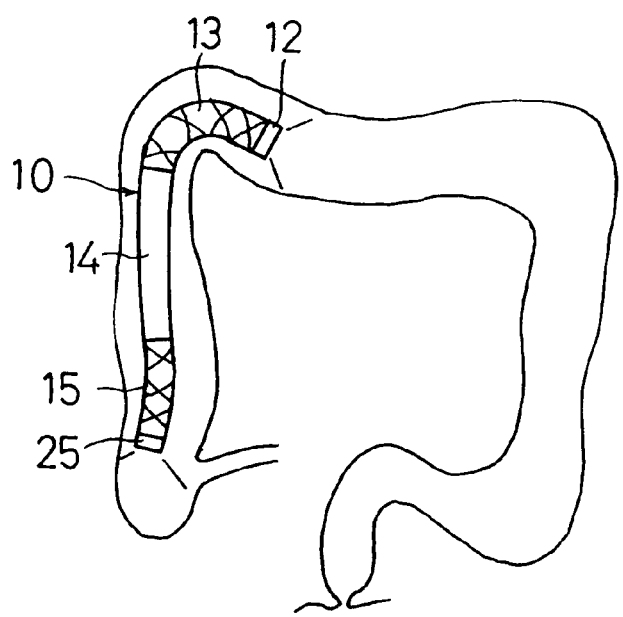
FIG. 10 is an explanatory view of the rod-shaped endoscope body shown in FIGS. 5 and 6 which is positioned in the large intestine, showing a state where the rod-shaped endoscope body proceeds within the large intestine.
Figure 11:
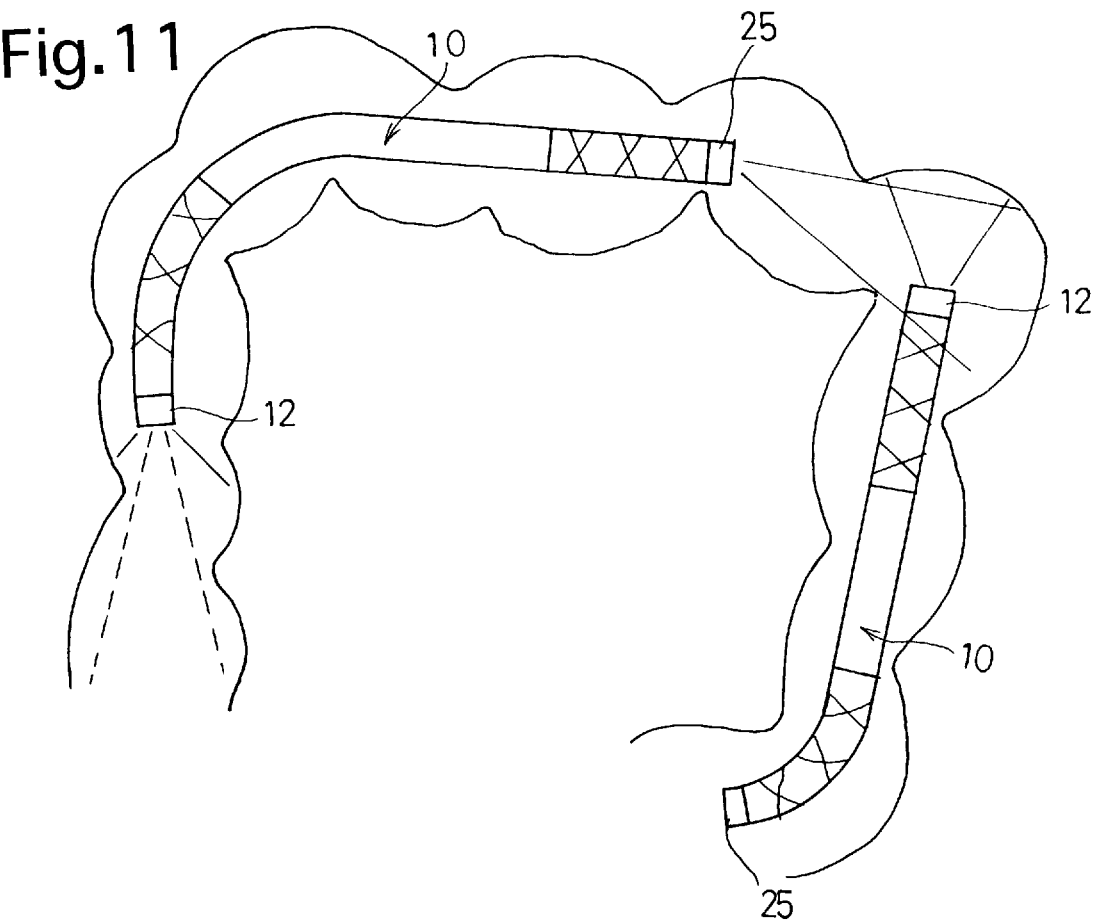
FIG. 11 is an explanatory view of the rod-shaped endoscope body shown in FIGS. 5 and 6 which is positioned in the large intestine, illustrating how the blind spots that occur with the front observing system can be substantially reduced via observation by the rear observing system, while the blind spots that occur with the rear observing system can be substantially reduced via observation by the front observing system.

With the second hard portion 25 having a structure mentioned above, the operator can observe the target inner part of the body by bending the second bending portion 15. Similar to the case shown in FIG. 8 in the first embodiment of the rod-shaped endoscope body 10, the second bending portion 15, which is positioned at the rear end of the rod-shaped endoscope body 10, can be fixed to an inner wall of the esophagus by bending the second bending portion 15 (see FIG. 9). Furthermore, in the case as shown in FIG. 10 where the second embodiment of the rod-shaped endoscope body 10 is in the large intestine or in the case as shown in FIG. 11 where the same is introduced to the large intestines via the anus, the blind spots that occur with the front hard portion 12 can be substantially reduced via observation by the rear hard portion 25, while the blind spots that occur with the rear hard portion 25 can be substantially reduced via observation by the front hard portion 12.

Figure 13:
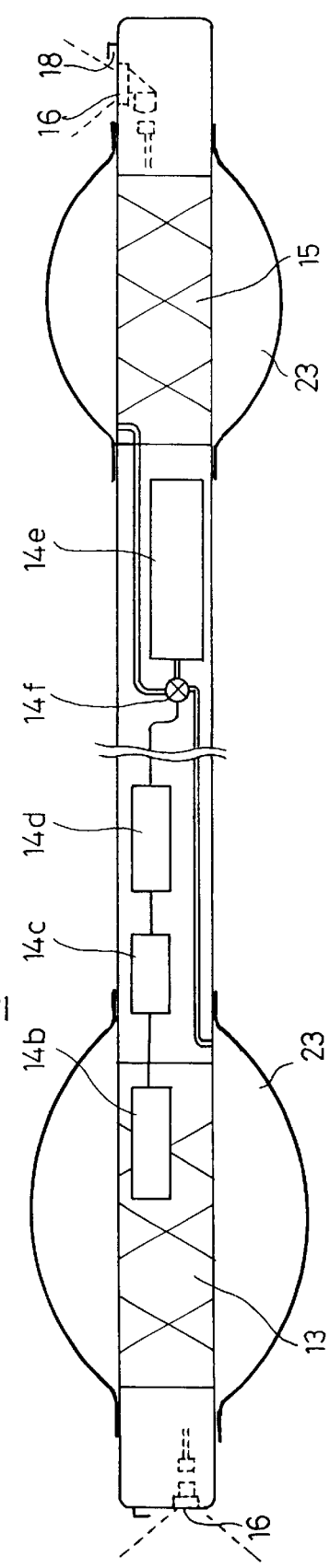
FIG. 13 is a schematic cross sectional view of the third embodiment of the rod-shaped endoscope body, according to the present invention.
Figure 14:
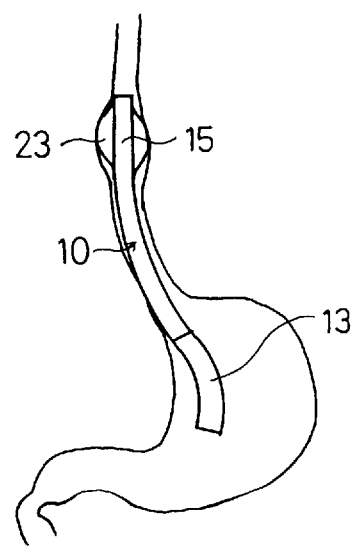
FIG. 14 is an explanatory view of the rod-shaped endoscope body shown in FIG. 13 which is positioned between the esophagus and the stomach, showing a state where the rod-shaped endoscope body is fixed to the inside of the esophagus by inflating a balloon provided at the rear end of the rod-shaped endoscope body.
Figure 15:
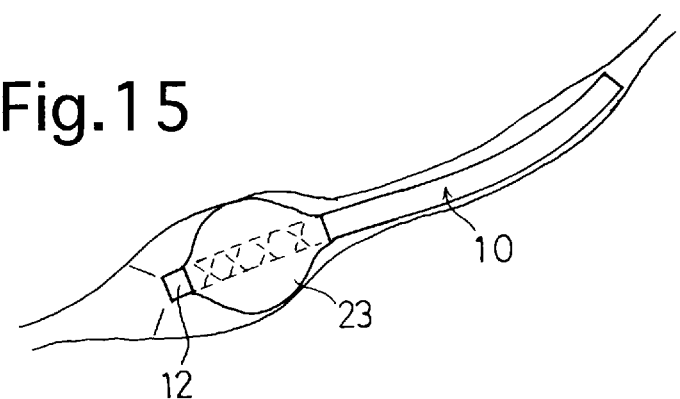
FIG. 15 is an explanatory view of the rod-shaped endoscope body shown in FIG. 13 which is positioned in a tubular passage in a body, showing a state where the rod-shaped endoscope body is fixed to the inner wall of the tubular passage by inflating a balloon provided at the front end of the rod-shaped endoscope body.

FIG. 13 shows the third embodiment of the rod-shaped endoscope body 10 according to the present invention. The rod-shaped endoscope body 10 is provided with two balloons 23 respectively provided at the opposite ends of the rod-shaped endoscope body 10 as shown in FIG. 13. The rod-shaped endoscope body 10 can be provided with only one balloon 23 at either end. Each balloon 23 can be inflated by sending the compressed air in the compressed air tank 14e into the balloon 23, by operating the valve controlling portion 11h of the external device 11 so that the transmitter/receiver device 14b receives the radio operational signals transmitted from the external transmitting portion 11d, so as to operate the valve 14f. For instance, in the case where the third embodiment of the rod-shaped endoscope body 10 is in a tubular passage in a body, if the balloon 23 provided at the front end of the rod-shaped endoscope body 10 is inflated, the distance between the hard portion 12 and the inner wall of the tubular passage becomes large, which makes it easy to observe the inner wall of the tubular passage (see FIG. 15). Conversely, if the balloon 23 provided at the rear end of the rod-shaped endoscope body 10 is inflated, the rod-shaped endoscope body 10 can be held stably at a desired position in a case as shown in FIG. 14, the target inner part can be easily observed by manipulating the first bending portion 13.

The power supplying device 14c of the rod-shaped endoscope body 10 can be replaced by a built-in battery to simplify the structure of endoscopic system.

As can be understood from the foregoing, according to the fully-swallowable of endoscopic body of the present invention, since the rod-shaped endoscope body is entirely positioned in a body cavity without any cables or wires which connect the rod-shaped endoscope body with the external device, a patient to be examined does not suffer from pain even if the endoscope is retained in the patient's body for a long time. Furthermore, even if the rod-shaped endoscope body is in a body cavity having a inner wall which bends sharply, the target inner part can be easily observed since the rod-shaped endoscope body is provided with the front and rear bending portions 13 and 15, which reduces the blind spots of the rod-shaped endoscope body 10.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscopic system comprising:
a rod-shaped endoscope body which can be entirely swallowed by a patient to be examined so as to be located in a body cavity, said rod-shaped endoscope body including two bendable portions respectively positioned adjacent to opposite ends of said rod-shaped endoscope body and each being bendable along a curve of said body cavity; and
an external device provided separately from said rod-shaped endoscope body without a mechanical connection with said rod-shaped endoscope body;
said rod-shaped endoscope body comprising at least one light emitter; at least one observing system; a transmitter that transmits a radio wave which carries an image formed by said observing system; and a power supplying device,
said external device comprising a receiver that receives said radio wave which carries said image,
each said bendable portion comprising a bending portion that is configured to be bent by radio control from the external device so as to orient said at least one light emitter and said at least one observing system in a predetermined direction, and a flexible portion that is configured to be bent by an external force so as to bend said flexible portion along a curve of the body cavity, said bending portion being configured to be more flexible than said flexible portion.

2. The endoscopic system according to claim 1, said flexible portion being positioned between said two bendable portions to connect said two bendable portions, said rod-shaped endoscope body comprising a radio-controlled driving device which receives a radio signal transmitted from said external device to bend said bending portion in accordance with said radio operation signal, and
said external device includes an operational portion which is configured to transmit said radio signal to said radio-controlled driving device.

3. The endoscopic system according to claim 2, wherein said radio-controlled driving device comprises a plurality of drive wires made of a shape memory alloy, and a selective-heating device which selectively heats said plurality of drive wires to bend said bending portion.

4. The endoscopic system according to claim 1, wherein said rod-shaped endoscope body comprises more than one light emitter and more than one observing system which are positioned at different locations.

5. The endoscopic system according to claim 1, wherein said power supplying device comprises a built-in battery.

6. The endoscopic system according to claim 1, wherein said external device comprises a microwave transmitter that transmits a microwave to said rod-shaped endoscope body, and wherein said power supplying device converts said microwave into electrical current to supply said electrical current to said rod-shaped endoscope body.

7. The endoscopic system according to claim 1, wherein said observing system comprises an objective optical system and a CCD image sensor.

8. The endoscopic system according to claim 1, wherein said external device comprises a monitor which visually indicates said image.

9. The endoscopic system according to claim 1, said bending portion comprising a plurality of adjacently positioned articulated joints.

10. The endoscopic system according to claim 1, said flexible portion being bendable along a curve of the body cavity independently of said external device.

11. An endoscopic system comprising:

a rod-shaped endoscope body comprising a first bending portion, a flexible portion and a second bending portion which are arranged in that order; and a radio controller for manipulating each of said first and second bending portions so as to bend by radio-control;

said rod-shaped endoscope body comprising at least one light emitter that illuminates a target inner part of a living body;

at least one image pick-up device that takes an image of said target inner part illuminated by said at least one light emitter; and a transmitter that transmits a radio wave which carries said image taken by said image pick-up device, each of said first and second bending portions being configured to be bent by radio control from said radio controller so as to orient said at least one light emitter and said at least one observing system in a predetermined direction, said flexible portion being configured to be bent by an external force so as to bend said flexible portion along a curve of the body cavity, each of said first and second bending portions being configured to be more flexible than said flexible portion.

12. The endoscopic system according to claim 11, wherein said rod-shaped endoscope body further comprises a first hard portion fixed to one of the opposite ends of said rod-shaped endoscope body, and wherein one of said at least one light emitter and one of said at least one image pick-up device are fixed to said first hard portion.

13. The endoscopic system according to claim 12, wherein said rod-shaped endoscope body further comprises a second hard portion fixed to another of the opposite ends of said rod-shaped endoscope body, and wherein another of said at least one light emitter and another of said at least one image pick-up device are fixed to said second hard portion.

14. The endoscopic system according to claim 11, wherein said radio controller comprises a monitor and a receiver that receives said radio wave to indicate said image on said monitor.

15. The endoscopic system according to claim 11, wherein said radio controller further comprises a second transmitter that transmits a microwave to said rod-shaped endoscope body, and wherein said rod-shaped endoscope body is provided therein with a power supplying device which receives said microwave to convert said microwave into electrical current which is to be used as a power source of said rod-shaped endoscope body.

16. The endoscopic system according to claim 11, said bending portion comprising a plurality of adjacently positioned articulated joints.

17. The endoscopic system according to claim 11, said flexible portion being bendable along a curve of the body cavity independently of said external device.

18. A endoscope system comprising:

a rod-shaped endoscope body which can be swallowed by a patient to be examined, so as to be located in a body cavity, said rod-shaped endoscope body including two bendable portions respectively positioned adjacent opposite ends of said rod-shaped endoscope body and each being bendable along a curve of said body cavity;

said rod-shaped endoscope body comprising at least one light emitter, at least one observing system, a transmitter that transmits a radio wave which carries an image formed by said observing system, and a power supplying device;

said bendable portion comprising a bending portion that is configured to be bent by radio control from an external device so as to orient said at least one light emitter and said at least one observing system in a predetermined direction, and a flexible portion that is configured to be bent by an external force so as to bend said flexible portion along a curve of the body cavity, said bending portion being configured to be more flexible than said flexible portion; and said rod-shaped endoscope body comprising a radio-controlled driving device which is configured to receive a radio operation signal transmitted from the external device to bend said bending portion in accordance with the radio operation signal.

19. The endoscope system according to claim 18, said flexible portion being bendable along a curve of the body cavity independently of a signal received by said radio-controlled driving device.

* * * * *